(12) United States Patent
Wang

(10) Patent No.: US 8,293,260 B2
(45) Date of Patent: Oct. 23, 2012

(54) ELASTOMERIC COPOLYMER COATINGS CONTAINING POLY (TETRAMETHYL CARBONATE) FOR IMPLANTABLE MEDICAL DEVICES

(75) Inventor: Yunbing Wang, Sunnyvale, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1193 days.

(21) Appl. No.: 11/810,652

(22) Filed: Jun. 5, 2007

(65) Prior Publication Data
US 2008/0306592 A1 Dec. 11, 2008

(51) Int. Cl.
*A61F 13/00* (2006.01)
*A61F 2/00* (2006.01)
*A61F 2/06* (2006.01)

(52) U.S. Cl. ...... 424/422; 424/423; 623/1.15; 623/1.42; 623/1.46

(58) Field of Classification Search ............... None
See application file for complete search history.

(56) References Cited

U.S. PATENT DOCUMENTS

| | | |
|---|---|---|
| 3,687,135 A | 8/1972 | Stroganov et al. |
| 3,839,743 A | 10/1974 | Schwarcz |
| 3,900,632 A | 8/1975 | Robinson |
| 4,104,410 A | 8/1978 | Malecki |
| 4,110,497 A | 8/1978 | Hoel |
| 4,321,711 A | 3/1982 | Mano |
| 4,346,028 A | 8/1982 | Griffith |
| 4,596,574 A | 6/1986 | Urist |
| 4,599,085 A | 7/1986 | Riess et al. |
| 4,612,009 A | 9/1986 | Drobnik et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallstén et al. |
| 4,733,665 A | 3/1988 | Palmaz |
| 4,739,762 A | 4/1988 | Palmaz |
| 4,740,207 A | 4/1988 | Kreamer |
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |

(Continued)

FOREIGN PATENT DOCUMENTS
DE 44 07 079 9/1994
(Continued)

OTHER PUBLICATIONS

U.S. Appl. No. 10/317,435, filed Dec. 11, 2002, Hossainy et al.
(Continued)

*Primary Examiner* — Carlos Azpuru
*Assistant Examiner* — Casey Hagopian
(74) *Attorney, Agent, or Firm* — Squire Sanders (US) LLP

(57) ABSTRACT

Implantable medical devices with elastomeric copolymer coatings are disclosed.

24 Claims, 2 Drawing Sheets

U.S. PATENT DOCUMENTS

| | | |
|---|---|---|
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar et al. |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |

| | | | | | | |
|---|---|---|---|---|---|---|
| 6,103,230 A | 8/2000 | Billiar et al. | | 6,666,214 B2 | 12/2003 | Canham |
| 6,107,416 A | 8/2000 | Patnaik et al. | | 6,667,049 B2 | 12/2003 | Janas et al. |
| 6,110,188 A | 8/2000 | Narciso, Jr. | | 6,669,723 B2 | 12/2003 | Killion et al. |
| 6,113,629 A | 9/2000 | Ken | | 6,676,697 B1 | 1/2004 | Richter |
| 6,117,979 A | 9/2000 | Hendriks et al. | | 6,679,980 B1 | 1/2004 | Andreacchi |
| 6,120,536 A | 9/2000 | Ding et al. | | 6,689,375 B1 | 2/2004 | Wahlig et al. |
| 6,120,904 A | 9/2000 | Hostettler et al. | | 6,695,920 B1 | 2/2004 | Pacetti et al. |
| 6,121,027 A | 9/2000 | Clapper et al. | | 6,706,273 B1 | 3/2004 | Roessler |
| 6,125,523 A | 10/2000 | Brown et al. | | 6,709,379 B1 | 3/2004 | Brandau et al. |
| 6,127,173 A | 10/2000 | Eckstein et al. | | 6,719,934 B2 | 4/2004 | Stinson |
| 6,129,761 A | 10/2000 | Hubbell | | 6,719,989 B1 | 4/2004 | Matsushima et al. |
| 6,129,928 A | 10/2000 | Sarangapani et al. | | 6,720,402 B2 | 4/2004 | Langer et al. |
| 6,150,630 A | 11/2000 | Perry et al. | | 6,746,773 B2 | 6/2004 | Llanos et al. |
| 6,153,252 A | 11/2000 | Hossainy et al. | | 6,752,826 B2 | 6/2004 | Holloway et al. |
| 4,776,337 A | 12/2000 | Palmaz | | 6,753,007 B2 | 6/2004 | Haggard et al. |
| 6,159,951 A | 12/2000 | Karpeisky et al. | | 6,764,505 B2 | 7/2004 | Hossainy et al. |
| 6,160,084 A | 12/2000 | Langer et al. | | 6,818,063 B1 | 11/2004 | Kerrigan |
| 6,165,212 A | 12/2000 | Dereume et al. | | 6,846,323 B2 | 1/2005 | Yip et al. |
| 6,166,130 A | 12/2000 | Rhee et al. | | 7,166,099 B2 | 1/2007 | Devens, Jr. |
| 6,169,170 B1 | 1/2001 | Gryaznov et al. | | 2001/0044652 A1 | 11/2001 | Moore |
| 6,171,609 B1 | 1/2001 | Kunz | | 2002/0002399 A1 | 1/2002 | Huxel et al. |
| 6,174,330 B1 | 1/2001 | Stinson | | 2002/0004060 A1 | 1/2002 | Heublein et al. |
| 6,177,523 B1 | 1/2001 | Reich et al. | | 2002/0004101 A1 | 1/2002 | Ding et al. |
| 6,183,505 B1 | 2/2001 | Mohn, Jr. et al. | | 2002/0062148 A1 | 5/2002 | Hart |
| 6,187,045 B1 | 2/2001 | Fehring et al. | | 2002/0065553 A1 | 5/2002 | Weber |
| 6,210,715 B1 | 4/2001 | Starling et al. | | 2002/0111590 A1 | 8/2002 | Davila et al. |
| 6,224,626 B1 | 5/2001 | Steinke | | 2002/0116050 A1 | 8/2002 | Kocur |
| 6,228,845 B1 | 5/2001 | Donovan et al. | | 2002/0133183 A1 | 9/2002 | Lentz et al. |
| 6,240,616 B1 | 6/2001 | Yan | | 2002/0138133 A1 | 9/2002 | Lenz et al. |
| 6,245,076 B1 | 6/2001 | Yan | | 2002/0161114 A1 | 10/2002 | Gunatillake et al. |
| 6,245,103 B1 | 6/2001 | Stinson | | 2003/0033001 A1 | 2/2003 | Igaki |
| 6,248,344 B1 | 6/2001 | Ylanen et al. | | 2003/0065355 A1 | 4/2003 | Weber |
| 6,251,135 B1 | 6/2001 | Stinson et al. | | 2003/0093107 A1 | 5/2003 | Parsonage et al. |
| 6,251,142 B1 | 6/2001 | Bernacca et al. | | 2003/0100865 A1 | 5/2003 | Santini, Jr. et al. |
| 6,273,913 B1 | 8/2001 | Wright et al. | | 2003/0105518 A1 | 6/2003 | Dutta |
| 6,281,262 B1 | 8/2001 | Shikinami | | 2003/0105530 A1 | 6/2003 | Pirhonen et al. |
| 6,284,333 B1 | 9/2001 | Wang et al. | | 2003/0171053 A1 | 9/2003 | Sanders |
| 6,287,332 B1 | 9/2001 | Bolz et al. | | 2003/0187495 A1 | 10/2003 | Cully et al. |
| 6,290,721 B1 | 9/2001 | Heath | | 2003/0208259 A1 | 11/2003 | Penhasi |
| 6,293,966 B1 | 9/2001 | Frantzen | | 2003/0209835 A1 | 11/2003 | Chun et al. |
| 6,303,901 B1 | 10/2001 | Perry et al. | | 2003/0226833 A1 | 12/2003 | Shapovalov et al. |
| 6,312,459 B1 | 11/2001 | Huang et al. | | 2003/0236563 A1 | 12/2003 | Fifer |
| 6,327,772 B1 | 12/2001 | Zadno-Azizi et al. | | 2004/0093077 A1 | 5/2004 | White et al. |
| 4,733,665 C2 | 1/2002 | Palmaz | | 2004/0098095 A1 | 5/2004 | Burnside et al. |
| 6,375,826 B1 | 4/2002 | Wang et al. | | 2004/0111149 A1 | 6/2004 | Stinson |
| 6,379,381 B1 | 4/2002 | Hossainy et al. | | 2004/0127970 A1 | 7/2004 | Saunders et al. |
| 6,387,121 B1 | 5/2002 | Alt | | 2004/0143317 A1 | 7/2004 | Stinson et al. |
| 6,388,043 B1 | 5/2002 | Langer et al. | | 2004/0167610 A1 | 8/2004 | Fleming, III |
| 6,395,326 B1 | 5/2002 | Castro et al. | | 2005/0112170 A1* | 5/2005 | Hossainy et al. ............ 424/423 |
| 6,409,761 B1 | 6/2002 | Jang | | 2006/0093771 A1 | 5/2006 | Rypacek et al. |
| 6,423,092 B2 | 7/2002 | Datta et al. | | 2006/0095122 A1* | 5/2006 | Pacetti .................. 623/1.46 |
| 6,461,632 B1 | 10/2002 | Gogolewski | | 2007/0282435 A1* | 12/2007 | Wang et al. ............... 623/1.38 |
| 6,464,720 B2 | 10/2002 | Boatman et al. | | FOREIGN PATENT DOCUMENTS | | |
| 6,479,565 B1 | 11/2002 | Stanley | | | | |
| 6,485,512 B1 | 11/2002 | Cheng | | DE | 197 31 021 | 1/1999 |
| 6,492,615 B1 | 12/2002 | Flanagan | | DE | 198 56 983 | 12/1999 |
| 6,494,908 B1 | 12/2002 | Huxel et al. | | EP | 0 108 171 | 5/1984 |
| 6,495,156 B2 | 12/2002 | Wenz et al. | | EP | 0 144 534 | 6/1985 |
| 6,511,748 B1 | 1/2003 | Barrows | | EP | 0 364 787 | 4/1990 |
| 6,517,888 B1 | 2/2003 | Weber | | EP | 0 397 500 | 11/1990 |
| 6,527,801 B1 | 3/2003 | Dutta | | EP | 0 464 755 | 1/1992 |
| 6,537,589 B1 | 3/2003 | Chae et al. | | EP | 0 493 788 | 7/1992 |
| 6,539,607 B1 | 4/2003 | Fehring et al. | | EP | 0 554 082 | 8/1993 |
| 6,540,777 B2 | 4/2003 | Stenzel | | EP | 0 578 998 | 1/1994 |
| 6,554,854 B1 | 4/2003 | Flanagan | | EP | 0 604 022 | 6/1994 |
| 6,565,599 B1 | 5/2003 | Hong et al. | | EP | 0 621 017 | 10/1994 |
| 6,569,191 B1 | 5/2003 | Hogan | | EP | 0 623 354 | 11/1994 |
| 6,569,193 B1 | 5/2003 | Cox et al. | | EP | 0 665 023 | 8/1995 |
| 6,572,672 B2 | 6/2003 | Yadav et al. | | EP | 0 709 068 | 5/1996 |
| 6,574,851 B1 | 6/2003 | Mirizzi | | EP | 0 970 711 | 1/2000 |
| 6,585,755 B2 | 7/2003 | Jackson et al. | | GB | 2 247 696 | 3/1992 |
| 6,592,614 B2 | 7/2003 | Lenker et al. | | WO | WO 89/03232 | 4/1989 |
| 6,592,617 B2 | 7/2003 | Thompson | | WO | WO 90/01969 | 3/1990 |
| 6,613,072 B2 | 9/2003 | Lau et al. | | WO | WO 90/04982 | 5/1990 |
| 6,626,939 B1 | 9/2003 | Burnside et al. | | WO | WO 90/06094 | 6/1990 |
| 6,635,269 B1 | 10/2003 | Jennissen | | WO | WO 91/17744 | 11/1991 |
| 6,645,243 B2 | 11/2003 | Vallana et al. | | WO | WO 91/17789 | 11/1991 |
| 6,656,162 B2 | 12/2003 | Santini, Jr. et al. | | WO | WO 92/10218 | 6/1992 |
| 6,664,335 B2 | 12/2003 | Krishnan | | WO | WO 93/06792 | 4/1993 |

| | | |
|---|---|---|
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |
| WO | WO 2007/024500 | 3/2007 |
| WO | WO 2007/089435 | 8/2007 |
| WO | WO 2008/027107 | 3/2008 |
| WO | WO 2008/144418 | 11/2008 |

OTHER PUBLICATIONS

Acquarulo et al., *Enhancing Medical Device Performance with Nanocomposite Poly*, Med. Device Link, www.devicelink.com/grabber.php3?URL downloaded Mar. 26, 2007, 4 pgs.

Anonymous, *Bioabsorbable stent mounted on a catheter having optical coherence tomography capabilities*, Research Disclosure, Sep. 2004, pp. 1159-1162.

Ansari, *End-to-end tubal anastomosis using an absorbable stent*, Fertility and Sterility, vol. 32(2), pp. 197-201 (Aug. 1979).

Ansari, *Tubal Reanastomosis Using Absorbable Stent*, International Journal of Fertility, vol. 23(4), pp. 242-243 (1978).

Bull, *Parylene Coating for Medical Applications*, Medical Product Manufacturing News 18, 1 pg. (Mar. 1993).

Casper et al., *Fiber-Reinforced Absorbable Composite for Orthopedic Surgery*, Polymeric Materials Science and Engineering, vol. 53 pp. 497-501 (1985).

Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).

Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).

Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).

Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).

Devanathan et al., *Polymeric Conformal Coatings for Implantable Electronic Devices*, IEEE Transactions on Biomedical Engineering, vol. BME-27(11), pp. 671-675 (1980).

Elbert et al., *Conjugate Addition Reactions Combined with Free-Radical Cross-Linking for the Design of Materials for Tissue Engineering*, Biomacromolecules, vol. 2, pp. 430-441 (2001).

Hahn et al., *Biocompatibility of Glow-Discharge-Polymerized Films and Vacuum-Deposited Parylene*, J Applied Polymer Sci, vol. 38, pp. 55-64 (1984).

Hahn et al., *Glow Discharge Polymers as Coatings for Implanted Devices*, ISA, pp. 109-111 (1981).

He et al., *Assessment of Tissue Blood Flow Following Small Artery Welding with an Intraluminal Dissolvable Stent*, Microsurgery, vol. 19(3), pp. 148-152 (1999).

Kelley et al., *Totally Resorbable High-Strength Composite Material*, Advances in Biomedical Polymers, vol. 35, pp. 75-85 (1987).

Kubies et al., *Microdomain Structure in polylactide-block-poly(ethylene oxide) copolymer films*, Biomaterials, vol. 21, pp. 529-536 (2000).

Kutryk et al., *Coronary Stenting: Current Perspectives*, a companion to the Handbook of Coronary Stents, pp. 1-16 (1999).

Martin et al., *Enhancing the biological activity of immobilized osteopontin using a type-1 collagen affinity coating*, J. Biomed. Mater. Res., vol. 70A, pp. 10-19 (2004).

Mauduit et al., *Hydrolytic degradation of films prepared from blends of high and low molecular weight poly(DL-lactic acid)s*, J. Biomed. Mater. Res., vol. 30, pp. 201-207 (1996).

Middleton et al., *Synthetic biodegradable polymers as orthopedic devices*, Biomaterials, vol. 21, pp. 2335-2346 (2000).

Muller et al., *Advances in Coronary Angioplasty: Endovascular Stents*, Coron. Arter. Dis., vol. 1(4), pp. 438-448 (Jul./Aug. 1990).

nanoComposix, products, www.nanocomposix.com, downloaded Mar. 26, 2007, 2 pgs.

Nanosiliver, Photocatalyst and Nanocomposite Material, http://eng.nanocomposite.net downloaded Mar. 26, 2007, 1 pg.

Nichols et al., *Electrical Insulation of Implantable Devices by Composite Polymer Coatings*, ISA Transactions, vol. 26(4), pp. 15-18 (1987).

Peuster et al., *A novel approach to temporary stenting: degradable cardiovascular stents produced from corrodible metal-results 6-18 months after implantation into New Zealand white rabbits*, Heart, vol. 86, pp. 563-569 (2001).

Pietrzak et al., *Bioabsorbable Fixation Devices: Status for the Craniomaxillofacial Surgeon*, J. Craniofaxial Surg., vol. 2, pp. 92-96 (1997).

Pietrzak et al., *Bioresorbable implants—practical considerations*, Bone, vol. 19, No. 1, Supplement Jul. 1996, pp. 109S-119S.

Redman, *Clinical Experience with Vasovasostomy Utilizing Absorbable Intravasal Stent*, Urology, vol. 20(1), pp. 59-61 (Jul. 1982).

Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).

Schatz, *A View of Vascular Stents*, Circulation, vol. 79(2), pp. 445-457 (Feb. 1989).

Schmidt et al., *Long-Term Implants of Parylene-C Coated Microelectrodes*, Med & Biol Eng & Comp, vol. 26(1), pp. 96-101 (Jan. 1988).

Spagnuolo et al., *Gas 1 is induced by VE-cadherin and vascular endothelial growth factor and inhibits endothelial cell apoptosis*, Blood, vol. 103, pp. 3005-3012 (2004).

Tamai et al., *Initial and 6-Month Results of Biodegradable Poly-I-Lactic Acid Coronary Stents in Humans*, Circulation, pp. 399-404 (Jul. 25, 2000).

Tsuji et al., *Biodegradable Polymeric Stents*, Current Interventional Cardiology Reports, vol. 3, pp. 10-17 (2001).

Völkel et al., *Targeting of immunoliposomes to endothelial cells using a single -chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials, vol. 16, pp. 441-445 (1995).

Yau et al., Modern Size-Exclusion Liquid Chromatography, Wiley-Interscience Publication, IX-XV (1979).

International Search Report for PCT/US2008/064537, mailed Sep. 14, 2009, 7 pgs.

Desay, Microencapsulation and Related Drug Processes, title page and content 5 pgs total (1984).

Grulke et al., "Solubility Parameter Values", Polymer Handbook 4$^{th}$. Ed pp. 675-714 (1999).

Polymer Handbook 3$^{rd}$. Ed., Edited by Brandrup and Immergut, 31 pgs. 1989.

\* cited by examiner

ELASTOMERIC COPOLYMER COATINGS CONTAINING POLY (TETRAMETHYL CARBONATE) FOR IMPLANTABLE MEDICAL DEVICES

BACKGROUND OF THE INVENTION

1. Field of the Invention

This invention relates to elastomeric coatings for implantable medical devices.

2. Description of the State of the Art

This invention relates to radially expandable endoprostheses, which are adapted to be implanted in a bodily lumen. An "endoprosthesis" corresponds to an artificial device that is placed inside the body. A "lumen" refers to a cavity of a tubular organ such as a blood vessel.

A stent is an example of such an endoprosthesis. Stents are generally cylindrically shaped devices, which function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of the diameter of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

The treatment of a diseased site or lesion with a stent involves both delivery and deployment of the stent. "Delivery" refers to introducing and transporting the stent through a bodily lumen to a region, such as a lesion, in a vessel that requires treatment. "Deployment" corresponds to the expanding of the stent within the lumen at the treatment region. Delivery and deployment of a stent are accomplished by positioning the stent about one end of a catheter, inserting the end of the catheter through the skin into a bodily lumen, advancing the catheter in the bodily lumen to a desired treatment location, expanding the stent at the treatment location, and removing the catheter from the lumen.

In the case of a balloon expandable stent, the stent is mounted about a balloon disposed on the catheter. Mounting the stent typically involves compressing or crimping the stent onto the balloon. The stent is then expanded by inflating the balloon. The balloon may then be deflated and the catheter withdrawn. In the case of a self-expanding stent, the stent may be secured to the catheter via a constraining member such as a retractable sheath or a sock. When the stent is in a desired bodily location, the sheath may be withdrawn which allows the stent to self-expand.

The stent must be able to satisfy a number of mechanical requirements. First, the stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. Generally, it is desirable to minimize recoil. In addition, the stent must possess sufficient flexibility to allow for crimping, expansion, and cyclic loading. Longitudinal flexibility is important to allow the stent to be maneuvered through a tortuous vascular path and to enable it to conform to a deployment site that may not be linear or may be subject to flexure. Finally, the stent must be biocompatible so as not to trigger any adverse vascular responses.

The structure of a stent is typically composed of scaffolding that includes a pattern or network of interconnecting structural elements often referred to in the art as struts or bar arms. The scaffolding can be formed from wires, tubes, or sheets of material rolled into a cylindrical shape. The scaffolding is designed so that the stent can be radially compressed (to allow crimping) and radially expanded (to allow deployment). A conventional stent is allowed to expand and contract through movement of individual structural elements of a pattern with respect to each other.

Furthermore, it may be desirable for a stent to be biodegradable. In many treatment applications, the presence of a stent in a body may be necessary for a limited period of time until its intended function of, for example, maintaining vascular patency and/or drug delivery is accomplished. Therefore, stents fabricated from biodegradable, bioabsorbable, and/or bioerodable materials such as bioabsorbable polymers should be configured to completely erode only after the clinical need for them has ended.

Additionally, a medicated stent may be fabricated by coating the surface of either a metallic or polymeric scaffolding with a polymeric carrier that includes an active or bioactive agent or drug. Polymeric scaffolding may also serve as a carrier of an active agent or drug. Potential problems with therapeutic coatings for polymeric implantable medical devices, such as stents, include insufficient toughness, slow degradation rate, and poor adhesion.

SUMMARY OF THE INVENTION

Certain embodiments of the present invention include an implantable medical device comprising a coating above a polymer surface of the device, the coating comprising: a block copolymer including an elastic block and an anchor block, the elastic block being a homopolymer and elastomeric at physiological conditions, the anchor block being miscible with the surface polymer.

Further embodiments of the present invention include an implantable medical device comprising a coating above a polymer surface of the device, the coating comprising: a elastomeric copolymer including elastic units and anchor units, the elastic units providing elastomeric properties to the copolymer at physiological conditions, wherein the anchor units enhance adhesion of the coating with the surface polymer, wherein the copolymer is a star block copolymer having at least three arms, the arms comprising the elastic units and the anchor units.

DETAILED DESCRIPTION OF THE INVENTION

Various embodiments of the present invention include an implantable medical device with a coating having an elastomeric polymer above a polymeric surface of the device. The polymeric surface may be a surface of a polymer coating disposed above a substrate that can be composed of metal, polymer, ceramic, or other suitable material. Alternatively, the polymeric surface may be a surface of a polymeric substrate or body. "Above" a surface is defined as higher than or over a surface measured along an axis normal to the surface, but not necessarily in contact with the surface.

Figure 1:
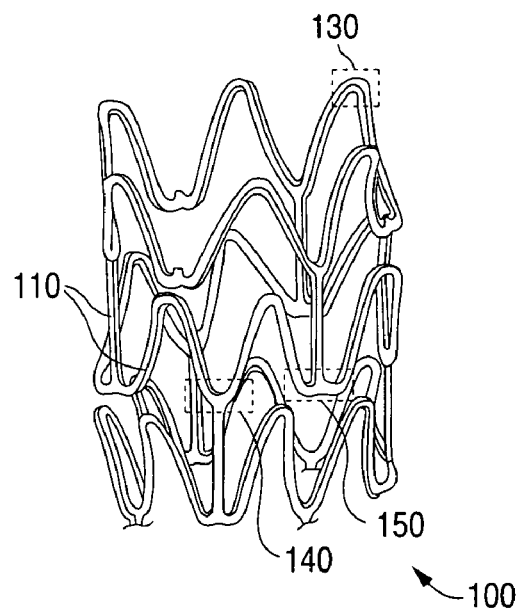
FIG. 1 depicts a view of a stent.

The present invention may be applied to implantable medical devices including, but not limited to, self-expandable stents, balloon-expandable stents, stent-grafts, and grafts (e.g., aortic grafts), and generally expandable tubular devices for various bodily lumen or orifices. A stent can have a scaffolding or a substrate that includes a pattern of a plurality of interconnecting structural elements or struts. FIG. 1 depicts a view of an exemplary stent 100. Stent 100 includes a pattern with a number of interconnecting structural elements or struts 110. In general, a stent pattern is designed so that the stent can be radially compressed (crimped) and radially expanded (to allow deployment). The stresses involved during compression and expansion are generally distributed throughout various structural elements of the stent pattern. The variations in stent patterns are virtually unlimited.

In some embodiments, a stent may be fabricated by laser cutting a pattern on a tube or a sheet rolled into a tube. Representative examples of lasers that may be used include, but are not limited to, excimer, carbon dioxide, and YAG. In other embodiments, chemical etching may be used to form a pattern on a tube.

An implantable medical device can be made partially or completely from a biodegradable, bioabsorbable, biostable polymer, or a combination thereof. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

As indicated above, a medicated implantable medical device, such as a stent, may be fabricated by coating the surface of the device with a drug. For example, a stent can have a coating including a drug dispersed in a polymeric carrier disposed over a substrate of the stent. Such a coating layer may be formed by applying a coating material to a substrate of an implantable medical device, such as a stent. The coating material can be a polymer solution and a drug dispersed in the solution. The coating material may be applied to the stent by immersing the stent in the coating material, by spraying the material onto the stent, or by other methods known in the art. The solvent in the solution is then removed, for example, by evaporation, leaving on the stent surfaces a polymer coating impregnated with the drug.

Stents are typically subjected to stress during use. "Use" includes manufacturing, assembling (e.g., crimping a stent on balloon), delivery of a stent through a bodily lumen to a treatment site, deployment of a stent at a treatment site, and treatment after deployment. Both the underlying scaffolding or substrate and the coating experience stress that result in strain in the substrate and coating. In particular, localized portions of the stent's structure undergo substantial deformation. For example, the apex regions of bending elements 130, 140, and 150 in FIG. 1 experience relatively high stress and strain during crimping, expansion, and after expansion of the stent.

Furthermore, polymer substrates and polymer-based coatings may be particularly vulnerable to mechanical instability during use of a stent. Such mechanical instability for coatings can include fracture and detachment from a substrate, for exampling, peeling. Some polymers may be susceptible to such mechanical instability due to insufficient toughness at high deformations. Additionally, detachment of coatings may be due to poor adhesion of the polymer-based coating to the substrate or another polymer layer. Therefore, polymer-based coatings are highly susceptible to tearing or fracture, and/or detachment, especially at regions subjected to relatively high stress and strain. Thus, it is important for a polymer-based coating to (1) be tough and have a high resistance to cracking and (2) have good adhesion with an underlying layer or substrate and to have a high resistance to detachment in the range of deformations that occur during crimping, during deployment of a stent, and after deployment.

As indicated above, a device may be composed in whole or in part of materials that degrade, erode, or disintegrate through exposure to physiological conditions within the body until the treatment regimen is completed. The device may be configured to disintegrate and disappear from the region of implantation once treatment is completed. The device may disintegrate by one or more mechanisms including, but not limited to, dissolution and chemical breakdown. The duration of a treatment period depends on the bodily disorder that is being treated. For illustrative purposes only, in treatment of coronary heart disease involving use of stents in diseased vessels, the duration can be in a range from about a month to a few years. However, the duration is typically in a range from about six to twelve months. Thus, it is desirable for polymer-based coatings and substrates of an implantable medical device, such as a stent, to have a degradation time at or near the duration of treatment. Degradation time refers to the time for an implantable medical device to substantially or completely erode away from an implant site.

Figure 2A:
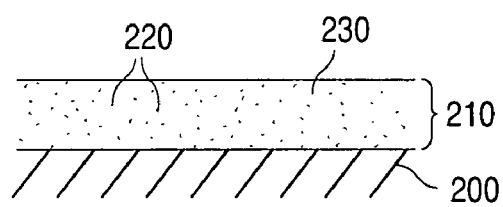
FIG. 2A depicts a cross-section of a stent surface with a block copolymer coating layer over a substrate.

Embodiments of the present invention can include an elastomeric polymer coating disposed over a polymer surface of a device, such as a stent scaffolding. In certain embodiments, the coating can be disposed directly over the surface of a polymer substrate of a device. FIG. 2A depicts a cross-section of a stent surface with an elastomeric polymer coating layer 210 over a substrate 200. In the embodiment shown in FIG. 2A, elastomeric polymer coating layer 210 includes a drug 220 dispersed in an elastomeric polymer 230. The substrate can be composed of a bioabsorbable polymer.

Figure 2B:
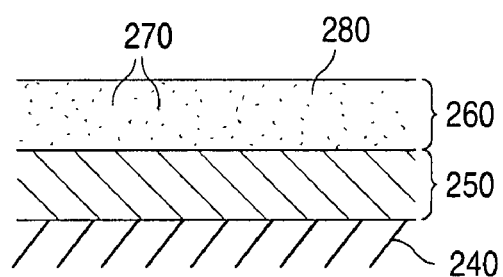
FIG. 2B depicts a cross-section of a stent surface with a block copolymer coating layer over a polymeric layer disposed over a substrate of the stent.

In other embodiments of the present invention, the elastomeric polymer coating can be over a polymer coating layer that is disposed over a substrate. FIG. 2B depicts a cross-section of a substrate 240 of a stent with a polymeric layer 250 disposed over substrate 240. An elastomeric polymer coating layer 260 is disposed over polymeric layer 250. Coating layer 260 includes a drug 270 dispersed within an elastomeric polymer 280. Polymeric layer 250 can be a primer layer for improving the adhesion of drug-polymer layer 260 to substrate 240. In the embodiment of FIG. 2B, substrate 240 can be metallic, polymeric, ceramic, or other suitable material.

In certain embodiments of the present invention, the elastomeric polymer coating can include a block copolymer having an elastic block and an anchor block. In such embodiments, the elastic block is a homopolymer that exhibits elastomeric or rubbery behavior at physiological conditions. In addition, the anchor block is miscible with the surface polymer and enhances the adhesion of the block copolymer coating with the surface polymer. In some embodiments, the elastic block, the anchor block, or both can be bioabsorbable polymers. In certain embodiments, all or a majority of the coating may be the block copolymer. Additionally, the coating can be a therapeutic layer with an active agent or drug mixed or dispersed within the block copolymer.

As mentioned above, the block copolymer coating exhibits rubbery or elastomeric behavior at physiological conditions. An "elastomeric" or "rubbery" polymer refers to a polymer that exhibits elastic deformation through all or most of a range of deformation. Physiological conditions include, but are not limited to, human body temperature, approximately 37° C. The elastic block of the block copolymer is an elastomeric or rubbery polymer that allows or provides the elastomeric or rubbery properties of the coating. Such elastomeric properties provide the coating with a high fracture toughness during use of a device such as a stent.

In some embodiments, the elastic blocks can have a glass transition temperature (Tg) below body temperature. Additionally, the block copolymer may be completely or substantially amorphous. Exemplary biodegradable polymers that are elastomeric or rubbery at physiological conditions include, but are not limited to, polycaprolactone (PCL), poly(tetramethyl carbonate) (PTMC), poly(4-hydroxy butyrate) (PHB), and polydioxanone (PDO).

As discussed above, the anchor block of the block copolymer can be miscible with the surface polymer. In one embodiment, the anchor block can have the same chemical composition as the surface polymer. Alternatively, the anchor block can have a chemical composition different from the surface polymer, but similar enough so that the anchor block is miscible with the surface polymer. In an exemplary embodiment, the block copolymer can have a PLLA anchor block and be disposed over a PLLA surface, which can be the surface of a PLLA substrate. In another exemplary embodiment, the block copolymer can have a PLLA anchor block and be disposed over a poly(L-lactide-co-glycolide) (LPLG) surface, which can be the surface of an LPLG substrate.

In certain embodiments, the anchor block can be a random copolymer. In such embodiments, the composition of the anchor block copolymer of the block copolymer coating can be selected so that the anchor block is miscible with the surface polymer. In addition, the units of the copolymer can be selected to adjust the degradation rate of the block copolymer. In one embodiment, the anchor block can include units that are more hydrolytically active or hydrophilic than other units to increase the degradation rate of the coating. In an exemplary embodiment, the anchor block can be LPLG. In such an embodiment, the surface polymer can be an LPLG copolymer. The composition of LLA and GA in the anchor block can be adjusted so that the LPLG anchor block is miscible with the LPLG surface polymer. In some embodiments, the surface polymer can be a copolymer having a high percentage of LLA units, for example, at least 60 wt %, 70 wt %, or 80 wt % LLA units.

In additional embodiments, the block copolymer can additionally include a fast degrading block that is selected to increases the degradation rate of the block copolymer coating. In some embodiment, the fast degrading blocks can be glassy at physiological conditions or have a Tg above body temperature. Additionally or alternatively, the fast degrading blocks can be immiscible with the surface polymer.

In some embodiments, the fast degrading block may have a higher degradation rate than the anchor block, the elastic block, or both. The fast degrading block may be composed of units that are more hydrophilic or more hydrolytically active than the elastic block or the anchor block. Additionally, fast degrading block may have acidic and hydrophilic degradation products. Since the rate of the hydrolysis reaction tends to increase as the pH decreases, acidic degradation products can increase the degradation rate of the block copolymer coating. Glycolide (GA) units, for example, have acidic degradation products which can increase the degradation rate of the coating. Exemplary fast degrading blocks can include poly(glycolide) (PGA) and LPLG that may not be miscible with a surface polymer.

In some embodiments, the toughness of the block copolymer coating can be adjusted by increasing or decreasing the weight percent of elastic blocks. As the weight percent of elastic blocks increases, the block copolymer can become more flexible and tougher. For example, for a PCL-b-PLLA coating, as the weight percent of PCL increases, the block copolymer becomes more flexible and tougher. The composition of the elastic blocks of the block copolymer can be greater than 20 wt %, 30 wt %, 40 wt %, 50 wt %, 60 wt %, 70 wt %, 80 wt %, 90 wt %, or greater than 90 wt % of the block copolymer.

In exemplary embodiments, the molecular weight of the elastic blocks can be between 20 kg/mol and 150 kg/mol, or greater than 150 kg/mol. The molecular weight of the anchor blocks can be between 20 kg/mol and 150 kg/mol, or greater than 150 kg/mol. The relative 20 weight percent of the elastic blocks and the anchor blocks can be between 1:5 and 10:1.

Additionally, in other embodiments, the degradation rate of the coating can be adjusted by increasing or decreasing the weight percent of fast degrading blocks. The degradation rate of the coating can be increased by increasing the weight percent of fast degrading blocks. For example, the weight percent of PGA in a PLLA-b-PGA-b-PDO block copolymer can be increased to increase the degradation rate of the polymer.

Embodiments of the block copolymer of the elastomeric coating can have two or more blocks. The block copolymer can be a diblock, triblock, tetrablock, pentablock, etc. copolymer. Diblock copolymers can include, for example, PLLA-b-PDO, PLLA-b-PCL, and PLLA-b-PTMC. Exemplary triblock copolymers include PLLA-b-PDO-b-PLLA, PLLA-b-PCL-PLLA, and PLLA-b-PTMC-b-PLLA, PLLA-b-PGA-b-PDO, etc. Such block copolymers may be suitable as coatings over a PLLA or LPLG surface.

In some embodiments, the block copolymer can be a branched polymer which corresponds to a polymer with "side chains." Branched polymers include, for example, hyperbranched-like polymers, comb-like polymers, star polymers, dendrimer-like star polymers, and dendrimers. A star polymer refers to a polymer having at least three chains or arms radiating outward from a common center. A dendritic polymer is a branched polymer resembling a tree-like structure. A comb structure corresponds to a linear polymer segment or backbone having a plurality of side chains extending outward from a position along the linear segment. In such embodiments, a block copolymer can be a branched polymer with at least one branch that is an elastic block and at least one branch that is an anchor block. The branched block copolymer can further include at least one branch that is a fast degrading block.

In these embodiments, the block copolymer can be a star block copolymer having at least three arms or branches with at least one arm being an elastic block and at least one arm being an anchor block. The star block copolymer can further include at least one arm that is a fast degrading block.

In further embodiments of the present invention, the elastomeric coating above a surface polymer of an implantable medical device can include a random copolymer with elastic units and anchor units. In such embodiments, the elastic units provide elastomeric or rubbery properties at physiological conditions to the random copolymer. "Elastic units," refer to monomer units that form elastic or rubbery polymers at physiological conditions. Exemplary elastic units can include, but are not limited to, caprolactone (CL), tetramethyl carbonate (TMC), 4-hydroxy butyrate (HB), and dioxanone (DO). In addition, the anchor units enhance the adhesion of the random copolymer coating with the surface polymer. In some embodiments, the elastic units, the anchor units, or both can be bioabsorbable. In certain embodiments, all or a majority of the coating may be the random copolymer. Additionally, the coating can be a therapeutic layer with an active agent or drug mixed or dispersed within the random copolymer.

Alternatively, the elastomeric copolymer can be an alternating copolymer with elastic units and anchor units alternating along the polymer chain. In addition, the elastomeric copolymer can include more than one type of elastic unit and more than one type of anchor unit.

The anchor units of the random copolymer are the same as at least one unit in the surface polymer. Additionally, the anchor units can be miscible with the surface polymer. The anchor units can allow portions of segments of the random copolymer to be miscible with the surface polymer. The degree of adhesion can be increased by increasing the weight percent of the anchor units in the copolymer. In an exemplary embodiment, the surface polymer can be a crystalline or semicrystalline polymer. In such embodiments, the anchor units can be units of such a crystalline or semicrystalline polymer. In an exemplary embodiment, the random copolymer can have an LLA anchor units and be disposed over a PLLA surface, which can be the surface of a PLLA substrate. In another exemplary embodiment, the random copolymer can have a LLA, GA, or both LLA and GA anchor units and be disposed over an LPLG surface, which can be the surface of a LPLG substrate.

In additional embodiments, the random copolymer can additionally include fast degrading units, alternatively or additionally to anchor units, that are selected to increase the degradation rate of the random copolymer coating. The fast degrading units can be more hydrophilic or more hydrolytically active than the elastic units or the anchor units. Additionally, fast degrading blocks may have acidic and hydrophilic degradation products. The fast degrading units can be glassy at physiological conditions or can be different from units of the surface polymer. In an exemplary embodiment, GA units are fast degrading units in a random copolymer coating disposed over a PLLA surface polymer.

In some embodiments, the elastomeric copolymer can be a random or alternating copolymer of elastic units and fast degrading units. Alternatively, the copolymer can be a random or alternating copolymer of elastic units, anchor units, and fast degrading units.

Exemplary random copolymer coatings include PLLA-co-PDO, PLLA-co-PCL, PLLA-co-PTMC, PLLA-co-PDO-co-PTMC, PLLA-co-PGA-co-PDO, PLLA-co-PGA-co-PCL, PLLA-co-PGA-co-PTMC, etc. Such block copolymers may be suitable as coatings over a PLLA or LPLG surface.

In some embodiments, the random copolymer can be a branched polymer, including, for example, hyperbranched-like polymers, comb-like polymers, star polymers, dendrimer-like star polymers, and dendrimers. In such embodiments, the random copolymer can be a random branched copolymer having branches including elastic units and anchor units. The branches of branched polymers can further include fast degrading units. In exemplary embodiments, the random copolymer can be a random star copolymer having at least three arms or branches with at least one arm including elastic units and anchor units. The arms can also include fast degrading units.

Embodiments of the elastomeric polymer coating of the present invention can be applied to a polymer surface so that at least some of the elastomeric polymer is mixed with the surface polymer. In particular, at least the anchor blocks of the block copolymer coating can be mixed within the surface polymer. Alternatively, segments of the random copolymer of the random copolymer coating that include anchor units can be mixed with the surface polymer. It is believed that an interfacial region between the coating and the surface polymer can form with elastomeric polymer mixed with surface polymer. The anchor blocks of the block copolymer or the anchor units of the random copolymer can act as a compatibilizer that strengthens the bond between the coating and the coated surface. The interfacial region can enhance the adhesion of the elastomeric polymer coating to the polymer substrate or a polymer surface layer, in general.

Figure 3:
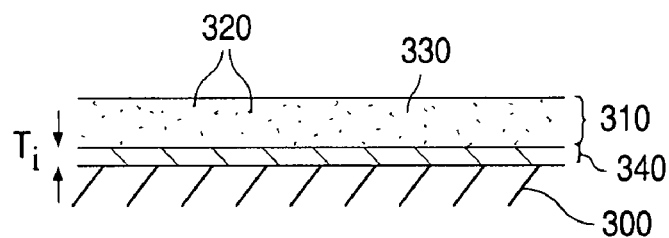
FIG. 3 depicts a cross-section of a stent surface with the block-copolymer coating layer over a substrate of the stent showing an interfacial region.

FIG. 3 depicts a cross-section of a stent surface with an elastomeric copolymer coating layer 310 over a substrate 300. Coating layer 310 can be applied to form an interfacial region 340 which can include anchor blocks or random copolymer segments including anchor units mixed with substrate polymer. A drug 320 can be mixed or dispersed within coating layer 310 and interfacial region 340. A thickness Ti of interfacial region 340 can be varied depending on coating application processing parameters.

The enhanced adhesion can allow the use of a tough, high fracture resistant coating that may otherwise have poor adhesion to a polymer substrate of a device. The polymer material for a substrate of a device, such as a stent, may be selected primarily on the basis of strength and stiffness so that the stent substrate can provide support for a lumen. Such substrate polymers can be crystalline or semi-crystalline polymers that are glassy or have a Tg above body temperature. Tough, elastomeric polymers may not necessarily have good adhesion with such a substrate. Embodiments of the block copolymer or random copolymer disclosed herein allow the use of a tough, high fracture resistant coating over a glassy substrate. Such glassy substrate polymers include PLLA and LPLG.

In some embodiments, the block copolymer coating can include a dispersed polymer phase. In such embodiments, the anchor block can have a high enough molecular weight that a dispersed anchor block phase is formed within an elastomeric phase composed of the elastic blocks. In these embodiments, the anchor block can be a crystalline or semicrystalline polymer. The dispersed phase can be crystalline or semi-crystalline polymer regions that are dispersed within an amorphous elastomeric phase. The crystalline regions can be used to modify the delivery rate of a dispersed drug from the coating. The crystalline regions tend to increase the delivery rate of drug from the coating.

Embodiments of the elastomeric polymers disclosed herein can be formed by solution-based polymerization.

Other methods of forming the elastomeric polymers are also possible, such as, without limitation, melt phase polymerization.

Some embodiments of the solution polymerization involve forming the elastic blocks first and then the anchor blocks. In such embodiments, a solution is prepared including the elastic units for the elastic blocks, an appropriate solvent, an appropriate initiator, and catalyst. The elastic blocks are formed in the solution from the monomers. The anchor block units for the anchor block and catalyst are then added to the solution to form anchor blocks that are bonded to the elastic blocks. The elastomeric block copolymer can be removed from the solution through precipitation in a non-solvent of the elastomeric block copolymer. The solvent(s) for the reaction mixture can be selected so that the elastic blocks formed are soluble in the solvent(s) to allow the elastic blocks to copolymerize with anchor blocks in solution.

For example, to prepare PDO-b-PLLA diblock copolymer, PDO elastic blocks are formed in a solution containing DO monomers, a dodecanol initiator, and stannous octoate catalyst in a toluene solvent. L-lactide monomers are then added to the solution. The L-lactide monomers react with PDO to form PDO-b-PLLA. The solution can then be added to methanol, which is a non-solvent for the formed block copolymer, to precipitate the elastomeric block copolymer from solution. Other embodiments of the solution polymerization involve forming the anchor blocks first and then the elastic blocks.

In other embodiments of solution polymerization, elastomeric block copolymers can be formed by reacting elastic blocks swollen with a solvent that contain anchor block monomer units. The elastic blocks are swollen by a solvent after they are formed so that they can react with anchor block monomer units. One of skill in the art can select a solvent that swells but does not dissolve the elastic blocks.

The elastomeric random copolymer can be prepared by solution polymerization by preparing a solution including the elastic units, anchor units, optionally fast degrading units, an appropriate solvent, an appropriate initiator, and catalyst. The mixture is allowed to react to form the elastomeric random copolymer. The elastomeric random copolymer can be removed from the solution through precipitation in a non-solvent of the elastomeric random copolymer.

For example, to prepare a PLLA-co-PCL-co-PDO random copolymer, a solution is formed containing DO units, CL units, and LLA units, a dodecanol initiator, and stannous octoate catalyst in a toluene solvent. The monomers react to form the random copolymer. The solution can then be added to methanol, which is a non-solvent for the formed random copolymer, to precipitate the elastomeric random copolymer from solution.

In one embodiment, the solvent for use in synthesizing the elastomeric block copolymer is devoid of alcohol functional groups. Such alcohol groups may act as initiators for chain growth in the polymer. Solvents used to synthesize the elastomeric block copolymer include, but are not limited to, chloroform, toluene, xylene, and cyclohexane.

Elastomeric star block copolymers and random copolymers can be synthesized according to the schemes described above by using an appropriate initiator. In one embodiment, pentaerythritol can be used as an initiator to synthesize star polymers.

Embodiments of the elastomeric polymer coating of the present invention may be formed over an implantable medical device, such as a stent, by applying a coating material to a polymer surface of the device. The coating material can be a solution including the elastomeric copolymer. The solution can further include an active agent or drug dissolved in a solvent. As discussed above, the coating material may be applied to the stent by immersing the device in the coating material, by spraying the composition onto the device, or by other methods known in the art. The solvent in the applied solution is removed, leaving on the device surfaces the elastomeric polymer coating and optionally drug dispersed within the polymer.

Drying or solvent removal can be performed by allowing the solvent to evaporate at room or ambient temperature. Depending on the volatility of the particular solvent employed, the solvent can evaporate essentially upon contact with the stent. Alternatively, the solvent can be removed by subjecting the coated stent to various drying processes. Drying time can be decreased to increase manufacturing throughput by heating the coated stent. For example, removal of the solvent can be induced by baking the stent in an oven at a mild temperature (e.g., 50° C.) for a suitable duration of time (e.g., 2-4 hours) or by the application of warm air. In an embodiment, a substantial portion of solvent removed may correspond to less than 5%, 1%, or more narrowly, less than 0.5% of solvent remaining after drying. Depositing a coating of a desired thickness in a single coating stage can result in an undesirably nonuniform surface structure and/or coating defects. Therefore, a coating process can involve multiple repetitions of application, for example, by spraying a plurality of layers.

In some embodiments, the solvent of the coating material is also a solvent for the surface polymer on which the coating material is applied. Specifically, a "solvent" for a given polymer can be defined as a substance capable of dissolving or dispersing the polymer or capable of at least partially dissolving or dispersing the polymer to form a uniformly dispersed mixture at the molecular- or ionic-size level. The solvent should be capable of dissolving at least 0.1 mg of the polymer in 1 ml of the solvent, and more narrowly 0.5 mg in 1 ml at ambient temperature and ambient pressure. The solvent in the coating material can dissolve at least a portion of the surface polymer upon application of the coating material to the polymer surface.

Due to dissolution of a portion of the surface polymer, the coating material near the surface of the surface polymer includes dissolved surface polymer in addition to the elastomeric polymer from the coating material. It is believed that upon removal of the solvent, an interfacial region, as depicted in FIG. 3, is formed that includes anchor blocks of the block copolymer or segments of the random copolymer mixed with surface polymer. This interfacial region can be formed due to the miscibility of the surface polymer with the anchor blocks or segments including anchor units.

In other embodiments, the solvent in the coating material can be capable of swelling the surface polymer, but is incapable or substantially incapable of dissolving the surface polymer. A solvent that is capable of swelling the surface polymer and is incapable or substantially incapable of dissolving the polymer is understood to mean a sample of the surface polymer swells when immersed in the solvent and the swollen sample of the surface polymer remains in the solvent with a negligible loss of mass for an indefinite period of time at conditions of ambient temperature and pressure.

Solvents for polymers can be found in standard texts (e.g., see Fuchs, in Polymer Handbook, 3rd Edition and Deasy, Microencapsulation and Related Drug Processes, 1984, Marcel Dekker, Inc., New York.) The ability of a polymer to swell and to dissolve in a solvent can be estimated using the Cohesive Energy Density Concept (CED) and related solubility parameter values as discussed by Deasy and can be found in detail in the article by Grulke in Polymer Handbook.

Figure 4:
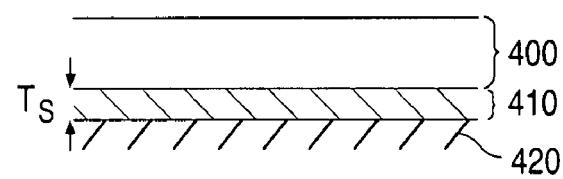
FIG. 4 depicts a cross-section of a stent showing a coating material layer over a swollen surface polymer layer.

FIG. 4 depicts a cross-section of a stent showing a coating material layer 400 over a swollen surface polymer layer 410. Swollen surface polymer layer 410 is over unswollen polymer coating layer or polymer substrate 420. As indicated above, unswollen surface polymer 420 can either be a substrate of the stent or a polymeric coating over a stent substrate. As shown, swollen surface polymer layer 410 has a thickness Ts. Due to swelling of the surface polymer in swollen surface polymer layer 410, it is believed that anchor blocks or segments containing anchor units of the elastomeric polymer in coating material layer 400 penetrate into or mix with the surface polymer in swollen polymer layer 410 prior to removal of the solvent. Upon removal of the solvent, a coating layer is formed over substrate 420.

Figure 5:
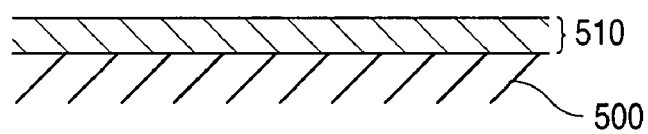
FIG. 5 depicts a polymer surface pretreated with a solvent.

In some embodiments, a polymeric substrate or polymeric surface coating layer can be pretreated with a solvent that dissolves or swells the surface polymer prior to applying a coating material. FIG. 5 depicts a layer 510 over a substrate or coating layer 500. Layer 510 can be a dissolved layer of surface polymer or a swollen layer of surface polymer. Following pretreatment, the coating material can be applied over the pretreated surface.

In certain embodiments, the coating material solvent is different from the pretreatment solvent. The use of a different solvent for the coating material and the pretreating can provide a degree of flexibility to the coating process. Generally, a treatment with a medicated stent may require a particular drug coating on a coating of a medicated stent. A drug may have an undesirably low or negligible solubility in a selected group of solvents that can dissolve or swell the surface polymer. Thus, a drug coating formed using such a solvent can have an undesirably low concentration of drug. A suitable pretreatment solvent can be used to dissolve or swell the surface polymer and a different solvent can be used as a coating solvent, in which the drug has an acceptable solubility. In general, a required solubility of a drug in a coating solvent is determined by the drug loading required of a particular treatment regimen. Specifically, it is desirable for a drug to have solubility of at least 1 wt % in a solvent for use as a coating material solvent for forming a drug-polymer layer on a stent.

Figure 6:
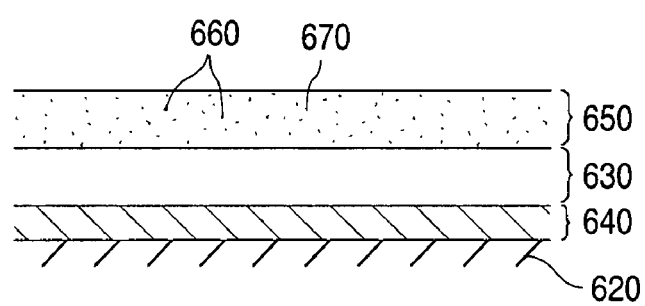
FIG. 6 depicts the cross-section of a stent surface with a drug-polymer layer over a block copolymer primer layer disposed over a substrate of the stent.

In other embodiments, an elastomeric polymer coating can be a primer layer over a polymer substrate or coating layer. The elastomeric polymer coating can act as a primer layer for a drug-polymer coating layer over the primer layer. The elastomeric polymer primer layer may be formed above a polymeric surface, as described above. The primer coating material can include an elastomeric polymer dissolved in a solvent that can dissolve or swell the surface polymer. A drug-polymer layer can then be formed over the elastomeric polymer primer layer. The drug coating material may include a polymer that is different from the elastomeric polymer and a solvent that is different from the primer coating material solvent. FIG. 6 depicts a drug layer 650 over primer coating layer 630. Drug layer 650 includes a drug 660 mixed or dispersed within a polymer 670. An interfacial layer 640, discussed above, includes anchor blocks or segments including anchor units and surface polymer.

In general, representative examples of polymers that may be used to fabricated a substrate of and coatings for an implantable device include, but are not limited to, poly(N-acetylglucosamine) (Chitin), Chitosan, poly(hydroxyvalerate), poly(lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(L-lactide-co-glycolide); poly(D,L-lactide), poly(caprolactone), poly(trimethylene carbonate), polyethylene amide, polyethylene acrylate, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose.

Additional representative examples of polymers that may be especially well suited for use in embodiments of the present invention include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATOFINA Chemicals, Philadelphia, Pa.), ethylene-vinyl acetate copolymers, and polyethylene glycol. For the purposes of the present invention, the following terms and definitions apply:

For the purposes of the present invention, the following terms and definitions apply:

The "glass transition temperature," Tg, is the temperature at which the amorphous domains of a polymer change from a brittle vitreous state to a solid deformable, ductile, or rubbery state at atmospheric pressure. In other words, the Tg corresponds to the temperature where the onset of segmental motion in the chains of the polymer occurs. When an amorphous or semicrystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition.

"Stress" refers to force per unit area, as in the force acting through a small area within a plane. Stress can be divided into components, normal and parallel to the plane, called normal stress and shear stress, respectively. True stress denotes the stress where force and area are measured at the same time. Conventional stress, as applied to tension and compression tests, is force divided by the original gauge length.

"Strength" refers to the maximum stress along an axis which a material will withstand prior to fracture. The ultimate strength is calculated from the maximum load applied during the test divided by the original cross-sectional area.

"Strain" refers to the amount of elongation or compression that occurs in a material at a given stress or load.

"Elongation" may be defined as the increase in length in a material which occurs when subjected to stress. It is typically expressed as a percentage of the original length.

"Toughness" is the amount of energy absorbed prior to fracture, or equivalently, the amount of work required to fracture a material. One measure of toughness is the area under a stress-strain curve from zero strain to the strain at fracture. Thus, a brittle material tends to have a relatively low toughness.

Drugs or therapeutic active agent(s) can include anti-inflammatories, antiproliferatives, and other bioactive agents.

An antiproliferative agent can be a natural proteineous agent such as a cytotoxin or a synthetic molecule. Preferably, the active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck) (synonyms of actinomycin D include dactinomycin, actinomycin IV, actinomycin $I_1$, actinomycin $X_1$, and actinomycin $C_1$), all taxoids such as taxols, docetaxel, and paclitaxel, paclitaxel derivatives, all olimus drugs such as macrolide antibiotics, rapamycin, everolimus, structural derivatives and functional analogues of rapamycin, structural derivatives and functional analogues of everolimus, FKBP-12 mediated mTOR inhibitors, biolimus, perfenidone, prodrugs thereof, co-drugs thereof, and combinations thereof. Representative rapamycin derivatives include 40-O-(3-hydroxy)propyl-rapamycin, 40-O-[2-(2-hydroxy)ethoxy]ethyl-rapamycin, or 40-O-tetrazole-rapamycin, 40-epi-(N1-tetrazolyl)-rapamycin (ABT-578 manufactured by Abbott Laboratories, Abbott Park, Ill.), prodrugs thereof, co-drugs thereof, and combinations thereof. In one embodiment, the anti-proliferative agent is everolimus.

An anti-inflammatory drug can be a steroidal anti-inflammatory agent, a nonsteroidal anti-inflammatory agent, or a combination thereof. In some embodiments, anti-inflammatory drugs include, but are not limited to, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus, pimecorlimus, prodrugs thereof, co-drugs thereof, and combinations thereof. In one embodiment, the anti-inflammatory agent is clobetasol.

Alternatively, the anti-inflammatory may be a biological inhibitor of proinflammatory signaling molecules. Anti-inflammatory biological agents include antibodies to such biological inflammatory signaling molecules.

In addition, drugs or active can be other than antiproliferative agents or anti-inflammatory agents. These active agents can be any agent which is a therapeutic, prophylactic, or a diagnostic agent. In some embodiments, such agents may be used in combination with antiproliferative or anti-inflammatory agents. These agents can also have anti-proliferative and/or anti-inflammatory properties or can have other properties such as antineoplastic, antiplatelet, anti-coagulant, anti-fibrin, antithrombonic, antimitotic, antibiotic, antiallergic, antioxidant, and cystostatic agents. Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Some other examples of other bioactive agents include antibodies, receptor ligands, enzymes, adhesion peptides, blood clotting factors, inhibitors or clot dissolving agents such as streptokinase and tissue plasminogen activator, antigens for immunization, hormones and growth factors, oligonucleotides such as antisense oligonucleotides and ribozymes and retroviral vectors for use in gene therapy. Examples of antineoplastics and/or antimitotics include methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, thrombin inhibitors such as Angiomax™ (bivalirudin, Biogen, Inc., Cambridge, Mass.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), nitric oxide or nitric oxide donors, super oxide dismutases, super oxide dismutase mimetic, 4-amino-2,2,6, 6-tetramethylpiperidine-1-oxyl (4-amino-TEMPO), estradiol, anticancer agents, dietary supplements such as various vitamins, and a combination thereof. Examples of such cytostatic substance include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.). An example of an antiallergic agent is permirolast potassium. Other therapeutic substances or agents which may be appropriate include alpha-interferon, and genetically engineered epithelial cells. The foregoing substances are listed by way of example and are not meant to be limiting.

Other bioactive agents may include anti-infectives such as antiviral agents; analgesics and analgesic combinations; anorexics; antihelmintics; antiarthritics, antiasthmatic agents; anticonvulsants; antidepressants; antidiuretic agents; antidiarrheals; antihistamines; antimigrain preparations; antinauseants; antiparkinsonism drugs; antipruritics; antipsychotics; antipyretics; antispasmodics; anticholinergics; sympathomimetics; xanthine derivatives; cardiovascular preparations including calcium channel blockers and beta-blockers such as pindolol and antiarrhythmics; antihypertensives; diuretics; vasodilators including general coronary; peripheral and cerebral; central nervous system stimulants; cough and cold preparations, including decongestants; hypnotics; immunosuppressives; muscle relaxants; parasympatholytics; psychostimulants; sedatives; tranquilizers; naturally derived or genetically engineered lipoproteins; and restenoic reducing agents. Other active agents which are currently available or that may be developed in the future are equally applicable.

EXAMPLES

The examples set forth below are for illustrative purposes only and are in no way meant to limit the invention. The following examples are given to aid in understanding the invention, but it is to be understood that the invention is not limited to the particular materials or procedures of examples.

Example 1

PLLA-b-PDO Diblock Copolymer Synthesis

In this example, 10 g dioxanone (DO) and 10 g L-lactide (LLA) as monomers, 0.056 mL stannous octoate as catalyst, 0.15 ml dodecanol as initiator, and 50 ml toluene as solvent are used.

Step 1: One 500 ml three neck glassware reactor with a mechanical stirring rod is placed in a glove box which is filled with high purity nitrogen. The reactor is preheated to remove all moisture.
Step 2: DO, dodecanol, toluene, and stannous octoate are added into the reactor. The mixture is stirred at 100° C. for 48 hours.
Step 3: LLA is then added into the reactor and the reaction lasts for another 48 hours.
Step 4: 100 ml $CHCl_3$ is then added into the reactor to dilute the final product. Finally, the product solution is precipitated into 600 ml methanol, filtered out, and dried in vacuum at 80° C. until constant weight.

Example 2

PLLA-b-PDO-b-PLLA Triblock Copolymer Synthesis

In this example, 20 g dioxanone (DO) and 10 g L-lactide (LLA) as monomers, 0.084 mL stannous octoate as catalyst, 0.07 ml ethylene glycol as initiator and 70 ml toluene as solvent are used.

Step 1: One 500 three neck glassware reactor with a mechanical stirring rod is placed in a glove box which is filled with high purity nitrogen. The reactor is preheated to remove all moisture.
Step 2: DO, ethylene glycol, toluene, and stannous octoate are added into the reactor. The mixture is stirred at 100° C. for 48 hours.
Step 3: LLA is then added into reactor and the reaction lasts for another 48 hours.
Step 4: 100 ml $CHCl_3$ is then added into the reactor to dilute the final product. Finally, the product solution is precipitated into 600 ml methanol, filtered out, and dried in vacuum at 80° C. until constant weight.

Example 3

PLLA-co-PDO-co-PCL Random Copolymer Synthesis

In this example, 10 g dioxanone (DO), 10 g caprolactone (CL), and 10 g L-lactide (LLA) as monomers, 0.084 ml stannous octoate as catalyst, 0.22 ml dodecanol as initiator are used.

Step 1: One 500 three neck glassware reactor with a mechanical stirring rod is placed in a glove box which is filled with high purity nitrogen. The reactor is preheated to remove all moisture.
Step 2: DO, CL, LLA, initiator and catalyst are added into the reactor. The mixture is stirred at 110° C. for 40 hours.
Step 3: 200 ml $CHCl_3$ is then added into reactor to dissolve final product. Finally, the product solution is precipitated into 800 ml methanol, filtered out and dried in vacuum at 80° C. until constant weight.

Example 4

PLLA-co-PDO Star Copolymer Synthesis

Step 1: 15 g LLA and 15 g DO as monomers, 0.05 g pentaerythritol as initiator, and 100 ml toluene as solvent are added into a reactor free of moisture and oxygen.
Step 2: 60 mg stannous octoate catalyst is added after the temperature is increased to 100° C. and then stirred for 48 hours.
Step 3: 100 ml $CHCl_3$ is then added into reactor to dilute the final product. Finally, the product solution is precipitated into 600 ml methanol, filtered out, and dried in vacuum at 80° C. until constant weight.

Example 5

Preparation of Coating Solution and Coating Layer on PLLA Stent Backbone

The coating solution is prepared by mixing synthesized copolymer with drug in a solvent. Everolimus, Sirolimus, Paclitaxel, or their derivatives are used as drug, while acetone, dimethylene chloroform, or a mixture thereof is used as solvent. The weight ratio of copolymer to drug is in the range of 1:1 to 5:1, and the weight percent of copolymer in the solution is in the range of 0.1-4 wt %. The coating layer is prepared through spray/dip/drop coating of solution on stent backbone.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. An implantable medical device comprising a coating above a polymer surface of the device, the coating comprising:
   a block copolymer including an elastic block, an anchor block, and a fast degrading glassy block, the elastic block being a homopolymer and elastomeric at physiological conditions, the anchor block being miscible with the surface polymer, and the fast degrading glassy block having a faster degradation rate than the anchor block;
   wherein the elastic block is poly(tetramethyl carbonate); and
   wherein the anchor block comprises a polymer selected from the group consisting of poly(L-lactide) and poly(L-lactide-co-glycolide).

2. The device of claim 1, wherein the device is a stent.

3. The device of claim 1, wherein the surface polymer is poly(L-lactide) and the fast degrading glassy block is selected from the group consisting of poly(glycolide) and poly(L-lactide-co-glycolide).

4. The device of claim 1, wherein the block copolymer is biodegradable.

5. The device of claim 1, wherein a body of the device is formed from a biodegradable polymer.

6. The device of claim 1, wherein the block copolymer is a linear block copolymer.

7. The device of claim 1, wherein a majority of the coating comprises the block copolymer.

8. The device of claim 1, wherein the polymer surface comprises a surface of a substrate of the device or a surface of a coating layer above the substrate of the device.

9. The device of claim 1, wherein the coating comprises an active agent.

10. The device of claim 1, wherein the elastic block, the anchor block, and the surface polymer are biodegradable, and wherein the elastic block is faster degrading than the anchor block and the surface polymer.

11. The device of claim 1, wherein the anchor block is of the same chemical composition as the surface polymer.

12. The device of claim 1, wherein the anchor block and the surface polymer have a Tg above body temperature.

13. An implantable medical device comprising a coating above a polymer surface of the device, the coating comprising:
   an elastomeric copolymer including elastic units, anchor units, and fast degrading units, the elastic units providing elastomeric properties to the copolymer at physiological conditions and the fast degrading units being glassy and different from units of the surface polymer;
   wherein the anchor units enhance adhesion of the coating with the surface polymer;
   wherein the fast degrading units increase the degradation rate of the coating; and
   wherein the copolymer is a star copolymer having at least three arms, the arms comprising the elastic units, the fast degrading units, and the anchor units; and
   wherein the elastic units are poly(tetramethyl carbonate);
   wherein the surface polymer is poly(L-lactide); and
   wherein the anchor units are selected from the group consisting of lactide, glycolide, and combinations thereof.

14. The device of claim 13, wherein the device is a stent.

15. The device of claim 13, wherein the anchor units are the same as at least some units of the surface polymer.

16. The device of claim 13, wherein the star copolymer is a random copolymer or an alternating copolymer.

17. The device of claim 13, wherein the fast degrading units comprise glycolide.

18. The device of claim 13, wherein the anchor units of the star copolymer are biodegradable.

19. The device of claim 13, wherein a body of the device is formed from a biodegradable polymer.

20. The device of claim 13, wherein a majority of the coating comprises the elastomeric star copolymer.

21. The device of claim 13, wherein the polymer surface comprises a surface of a substrate of the device.

22. The device of claim 13, wherein the coating comprises an active agent.

23. The device of claim 13, wherein the anchor units are biodegradable.

24. The device of claim 13, wherein the polymer surface comprises a surface of a coating layer above the substrate of the device.

* * * * *